US010871477B2

(12) United States Patent
Graupmann et al.

(10) Patent No.: US 10,871,477 B2
(45) Date of Patent: Dec. 22, 2020

(54) CONTAMINANT CLEANING SYSTEMS AND RELATED METHODS USING ONE OR MORE REACTIVE SUBSTANCES, REACTION BYPRODUCT MEASUREMENTS, AND DIFFERENTIAL PRESSURE OR VACUUM TRANSFER OF THE REACTIVE SUBSTANCES AND REACTION BYPRODUCTS (71) Applicant: The United States of America as represented by the Secretary of the Navy, Crane, IN (US)

(72) Inventors: Mary M. Graupmann, Corona, CA (US); Christopher H. Clark, Riverside, CA (US); Michael L. Bishop, Norco, CA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 256 days.

(21) Appl. No.: 15/243,769

(22) Filed: Aug. 22, 2016

(65) Prior Publication Data
US 2017/0050223 A1 Feb. 23, 2017

Related U.S. Application Data (60) Provisional application No. 62/207,504, filed on Aug. 20, 2015.

(51) Int. Cl.
*H01J 37/32* (2006.01)
*B08B 9/027* (2006.01)
*G01N 33/00* (2006.01)

(52) U.S. Cl.
CPC ......... *G01N 33/0009* (2013.01); *B08B 9/027* (2013.01); *H01J 37/32862* (2013.01); *H01J 37/32981* (2013.01)

(58) Field of Classification Search
CPC ......... H01L 21/02041; H01L 21/02046; H01L 21/02057
See application file for complete search history.

(56) References Cited

U.S. PATENT DOCUMENTS

| 4,963,713 A * | 10/1990 | Horiuchi | H01J 37/32935 156/345.26 |
|---|---|---|---|
| 6,146,492 A * | 11/2000 | Cho | H01J 37/32935 118/715 |
| 2006/0158998 A1* | 7/2006 | Rinerson | B82Y 10/00 369/126 |
| 2008/0041819 A1* | 2/2008 | Kim | B08B 7/0035 216/67 |
| 2008/0251104 A1* | 10/2008 | Chen | C23C 16/4405 134/18 |
| 2011/0125331 A1* | 5/2011 | Fujii | H01L 21/67253 700/280 |
| 2013/0193108 A1* | 8/2013 | Zheng | C23C 14/54 216/59 |

* cited by examiner

*Primary Examiner* — Mikhail Kornakov
*Assistant Examiner* — Natasha N Campbell
(74) *Attorney, Agent, or Firm* — Naval Surface Warfare Center, Crane Division (57) ABSTRACT Contaminant cleaning systems and related methods are provided. Exemplary embodiments include a reactive substance generator to produce or transfer reactive substance(s) that react with contaminant(s) on an item into a cleaning chamber. An analysis section can be attached to the cleaning chamber to perform gas analysis on gas samples brought into the analysis chamber that measure reaction byproducts from the reactive substance(s) interaction with the contaminants. An exemplary valve system can selectively couple the reactive substance generator, the analysis section, and the cleaning chamber. An exemplary pumping system, in combination with the valve system, can selectively generate differential pressure/vacuum levels between the reactive substance generator vs cleaning chamber as well as between the cleaning chamber and analysis section. For example, the analysis chamber can be configured to have a higher vacuum than the cleaning chamber to facilitate passage of gas test samples into the analysis chamber.

10 Claims, 9 Drawing Sheets

ANALYSIS CHAMBER COMPONENTS

PUMPS AND THERMOCOUPLE GAUGE

FIG. 3

FIG. 4 VALVES AND PUMPS

FIG. 5 CONTROLLERS

CONTAMINANT CLEANING SYSTEMS AND RELATED METHODS USING ONE OR MORE REACTIVE SUBSTANCES, REACTION BYPRODUCT MEASUREMENTS, AND DIFFERENTIAL PRESSURE OR VACUUM TRANSFER OF THE REACTIVE SUBSTANCES AND REACTION BYPRODUCTS

CROSS-REFERENCE TO RELATED APPLICATIONS

The present application claims priority to U.S. Provisional Patent Application Ser. No. 62/207,504, filed Aug. 20, 2015, entitled "PLASMA CLEANING SYSTEM," the disclosure of which is expressly incorporated by reference herein.

STATEMENT REGARDING FEDERALLY SPONSORED RESEARCH OR DEVELOPMENT

The invention described herein was made in the performance of official duties by employees of the Department of the Navy and may be manufactured, used and licensed by or for the United States Government for any governmental purpose without payment of any royalties thereon. This invention (Navy Case 200,276) is assigned to the United States Government and is available for licensing for commercial purposes. Licensing and technical inquiries may be directed to the Technology Transfer Office, Naval Surface Warfare Center Corona, Calif.

BACKGROUND AND SUMMARY OF THE INVENTION

The present invention relates to a contaminant cleaning system. In particular, exemplary embodiments can include a reactive substance cleaning system and methods to provide a capability to generate or use activated reactants or reactive substances that chemically react with contaminants on or inside of items to be cleaned. Embodiments can also include a reactive substance or activated reactant transfer system using differential vacuum or pressure between multiple chambers to move the activated reactant or reactive substances or materials. Differential pressure can also be used to move reaction byproducts, reactions of the activated reactant, or reactive substances or materials that chemically react with the contaminants in a cleaning chamber into contact with analysis equipment. Control systems can be used to repeat cleaning cycles until a measured threshold or condition is met. Exemplary activated reactants or reactive materials, substances, or gas(es) can be low energy plasma, e.g., selected reactive gas or gas(es) comprising reactive materials including ionized reactive gases, free radicals, or other reactive substances that react with identified contaminants to result in a cleaning, contaminant reduction/removal, effect or outcome.

Existing cleaning systems use solvents comprised of hazardous materials as well as ozone depleting substances. Current methods employing solvents are incompatible with cleaning a wide variety of articles or items to be cleaned given such solvents damage such articles or items, thus it is desirable to eliminate or reduce use of such materials for industrial processes. Additionally, a variety of such existing cleaning systems are simply ineffective in providing desired cleaning. Moreover, a great deal of difficulty has been encountered in efforts to create alternatives to existing cleaning systems such as getting an alternative cleaning means inside items such as pressure gages due to lack of ease of access.

Accordingly, new contaminant cleaning systems and related methods are both needed and provided. Exemplary embodiments can include a reactive substance generator to produce or transfer reactive substance(s) that react with contaminant(s) on an item into a cleaning chamber. An analysis section can be attached to the cleaning chamber to perform gas analysis on gas samples brought into the analysis chamber that measure reaction byproducts from the interaction of reactive substance(s) with the contaminants. An exemplary valve system can selectively couple the reactive substance generator, the analysis section, and the cleaning chamber. An exemplary pumping system, in combination with the valve system, can selectively generate differential pressure/vacuum levels between the reactive substance generator vs cleaning chamber as well as between the cleaning chamber and analysis section. For example, the analysis chamber can be configured to have a higher vacuum than the cleaning chamber to facilitate passage of gas test samples into the analysis chamber.

For example, a plasma reactant cleaning system using cyclical differential pressure and vacuum levels which have testing means for determining when a desired level of cleaning has been achieved as well as related methods can be provided. Exemplary embodiments can include a plasma generator configured to generate low energy plasma from one or more cleaning gases or reactants selected to chemically react with contaminant materials to be removed from an article or item and deliver such resulting low energy cleaning plasma into a cleaning chamber. Byproduct gases will be formed in a cleaning chamber or in proximity to exposed surfaces (interior or exterior) of article or items to be cleaned when the cleaning or reactant plasma reacts with contaminant materials on exposed interior or exterior surfaces of an article or item. An exemplary analysis chamber can be attached to the cleaning chamber using, for example, a test sample input valve system and gas manifold(s). A gas analyzer can be coupled with the analysis chamber to perform gas analysis on samples of the byproduct gases that are brought into the analysis chamber through the test sample input valve system. A pumping system can be coupled with the analysis chamber and the cleaning chamber to provide a vacuum source for each chamber. Plasma cleaning or reactant gases and cleaning or reactant byproduct gases will move from one chamber or portion of the reactive substance cleaning system under comparatively higher pressure or lower vacuum level to another chamber or portion of the system under comparatively lower pressure or higher vacuum. The higher pressure cleaning or reactant gases moving into the lower pressure or higher vacuum area will expand to fill a volume of a given chamber or portion under lower pressure. In other words, in various embodiments the pumping system operates to generate low pressure or ultra-high vacuum levels in the cleaning chamber then the plasma that is generated at higher pressure and will flow into the lower pressure, higher vacuum cleaning chamber when directed by connecting valves, causing the reactive plasma cleaning gases to disperse within the void of the cleaning chamber and onto exposed surfaces of attached articles or items. The pumping system also operates to selectively and differentially generate low pressure or ultra-high vacuum levels in the analysis chamber and the cleaning chamber where the analysis chamber has a higher vacuum than the cleaning chamber during transfer cycles to facilitate passage of gas test samples into the analysis chamber. Exemplary embodiments of a cleaning system cycle reactive substances, e.g., gases as well as reaction byproducts by varying vacuum/pressure levels between sections of the system and thereby moves reaction byproducts, e.g., gases, from the cleaning chamber and/or article or item to be cleaned to the analysis section, including the gas analyzer, to perform testing as well. During or at completion of such transfer cycling, a gas analyzer coupled to the analysis chamber can perform testing to determine if cleaning or reactant byproduct gases are present at higher than levels that have been determined to be acceptable based on predetermined thresholds. Where such a byproduct gas threshold is not found to have been met or has exceeded or went past a selected value, then additional plasma cleaning or reactant gases can be introduced into the cleaning chamber by additional pressure/vacuum differential or transfer cycling to continue further reactions of cleaning/reactive substances such as reactive gas or gases (e.g., comprising ionized or activated reactants) with contaminant materials on surfaces of interest of such articles or items to be cleaned. Such cycling can be repeated until acceptable levels of byproduct gas or gases have been observed or measured based on, e.g. comparisons with such a reaction byproduct threshold(s). Multiple sources of reactive substances or materials can also be used with alternative embodiments of the invention along with different sequencing of such sources to achieve desired reaction based cleaning.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DRAWINGS

The embodiments of the invention described herein are not intended to be exhaustive or to limit the invention to precise forms disclosed. Rather, the embodiments selected for description have been chosen to enable one skilled in the art to practice the invention.

Various embodiments of a reactive substance cleaning system can provide one or more systems and processes to clean contaminants such as, e.g., hydrocarbons and other contaminants from exposed internal or external surfaces of articles or items, including exposed internal surfaces of Bourdon tubes and tubing. For example, reactant gas(es) is selected so that energized plasma formed from the reactant gas(es) will react with contaminant materials to be removed from articles or items. For example, a reactant gas such as oxygen can be converted with a plasma generator into a reactive substance comprising energetic oxygen ions and radicals which will react with hydrocarbon contaminants on surfaces of articles or items, producing carbon dioxide and water byproduct gases. Exemplary reactive substance cleaning system embodiments can utilize a remote plasma generator to provide reactive or cleaning gases comprising ionized reactant gas or gases to a system of interconnected chambers with isolation valves between them capable of creating, adjusting, and maintaining dissimilar pressure or vacuum transfer regions. An exemplary set of chambers can each be coupled to a vacuum generating system through valves to create dissimilar or disparate pressure or vacuum sections. Reactive substances, e.g., gas plasma flow can be directed by means of differential pressure or vacuum transfer cycling, e.g., within a cleaning chamber with an item or article to be cleaned connected to or disposed within, to expose exposed contaminated surfaces of such articles or items to reactive substances or cleaning gas(es) comprising, e.g., plasma or ionized reactive substances. Articles or items can have exterior or interior surfaces exposed to the reactive or cleaning gas(es) coupled with the cleaning chamber or alternatively an example where such articles or items are placed within the exemplary cleaning chamber. Reaction byproducts produced within the exemplary cleaning chamber can be analyzed using a gas analyzer to verify articles or items have been cleaned of surface contamination. Gas samples can be transferred between chambers or sections using similar differential pressure or vacuum transfer cycling to move post reaction or cleaning gas(es) out of the cleaning chamber and into the analyzer. Exemplary reactive substance cleaning systems can include equipment such as a reactive substance source generator (e.g., remote plasma generator), a gas analyzer section, ion gages to measure vacuum levels in various chambers or sections, a vacuum cleaning chamber, turbo pumps, scroll pump, valves, controllers, and a cooling system.

Figure 1:
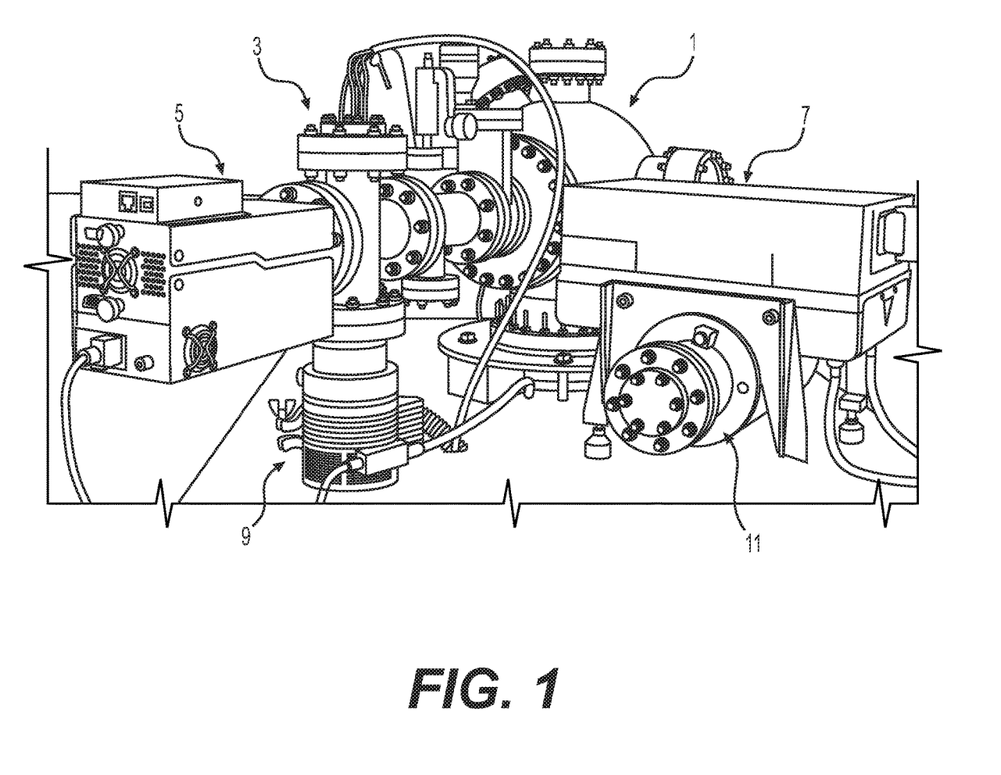
FIG. 1 shows one exemplary embodiment of a reactive substance cleaning system in accordance with one embodiment of the invention.

Referring to FIG. 1, a cleaning chamber 1, an analysis chamber 3, a gas analyzer 5, a plasma generator 7, a small turbo pumping mechanism 9, and input gas(es) (reactant and/or carrier gases) section 11 are shown as part of one embodiment of an exemplary a reactive substance cleaning system. An article or item to be cleaned can be attached or inserted into the cleaning chamber 1 for cleaning. The exemplary analysis chamber 3 can be configured to receive a sample of gases or environment from within the cleaning chamber 1 after reactive substances react with contaminants to perform monitoring and analysis by means of the gas analyzer 5. In at least some embodiments, reactive gas(es) comprising ionized reactant gas or gas(es) can be used to clean contaminants can be created from input gases 11 (e.g., reactant gas(es)) using, e.g., plasma generator 7). The small turbo pumping mechanism 9 can be used to provide an ultra-high vacuum (e.g., down to around $10^{-8}$ torr) within the analysis chamber 3 and analysis section (e.g., analysis chamber 3).

Figure 2:
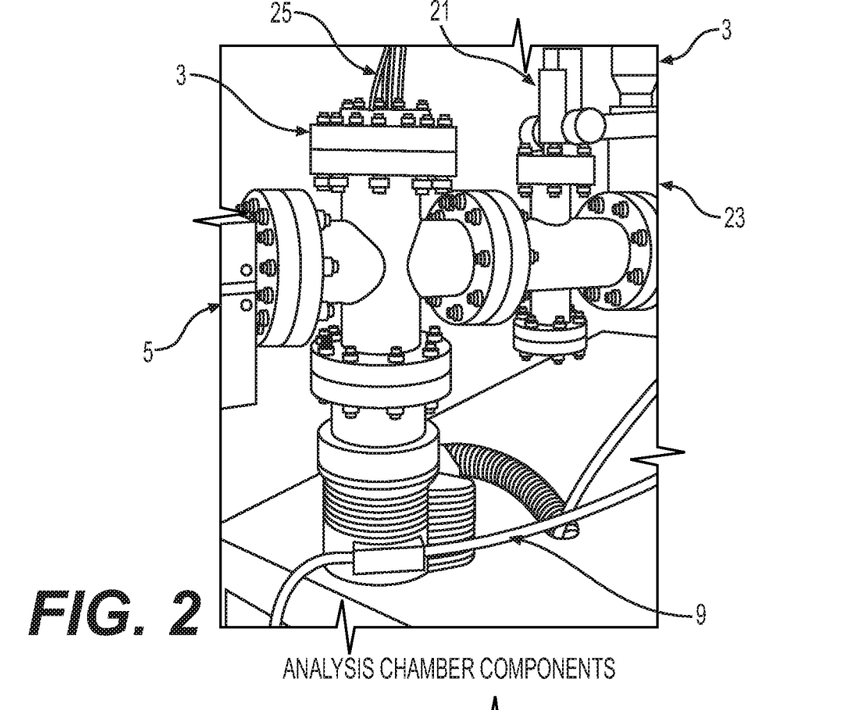
FIG. 2 shows an exemplary view of analysis chamber components used with one embodiment of the invention.

Referring to FIG. 2, an exemplary view of analysis chamber components used with one embodiment of the invention is shown. Exemplary analysis chamber 3 components include a leak valve 21, an ion gauge 25, a gate valve 23, and the small turbo pumping mechanism 9 coupled with a cooling system. The cooling system can include tubing which delivers cooled water into various pumps and plasma generator pump heat transfer manifolds or passageways (not shown) which can be coupled to a circulating chiller or cooling unit which passes cooled water through various components such as the small turbo pumping mechanism. The leak valve 21 can be used as a gas transport system to transport a gas sample from the cleaning chamber 1 environment to the analysis chamber 3. An ion gauge 25 assists with controlling parameters and monitoring environment conditions. The ion gauge 25 can be used to measure vacuum levels in the analysis chamber 3. A gate valve 23 can be used as part of a valve system to maintain and cycle pressure or vacuum levels between the cleaning chamber 1 and the analysis chamber 3 and permits gas flow from the cleaning chamber 1 into the analysis chamber 3 using, e.g. differential vacuum or pressure. In other words, cleaning chamber 1 containing the desired gas sample having a higher pressure, lower vacuum can be connected using gate valve 23 to a the analysis chamber that has a lower pressure, higher vacuum.

Figure 3:
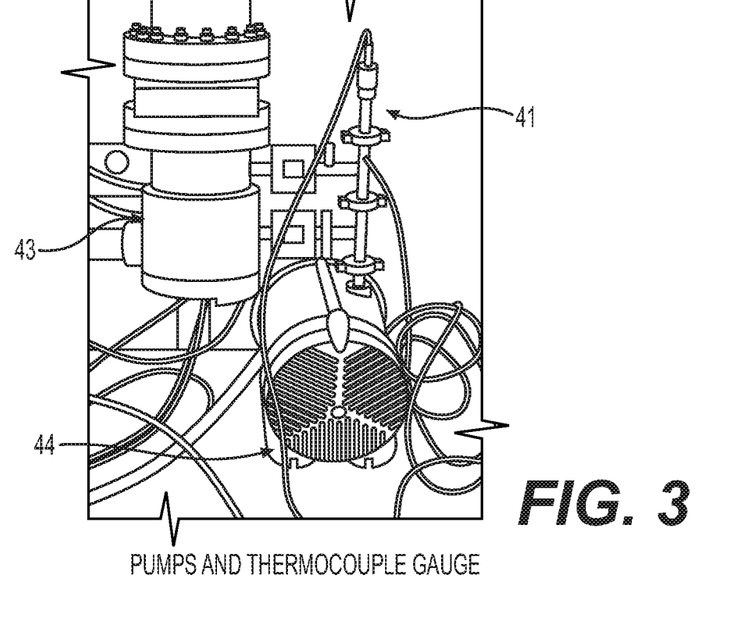
FIG. 3 shows an exemplary view of primary and secondary pumping mechanisms and a thermocouple gauge shown as part of one embodiment of the invention.

Referring to FIG. 3, primary and secondary pumping mechanisms, and a thermocouple gauge are shown as part of one exemplary plasma cleaning system. A thermocouple gauge 41 can be used to control parameters and monitor environment conditions. A large turbo pumping mechanism 43 and a roughing pumping mechanism 44 can provide a source of differential pressure or vacuum for various sections of an exemplary cleaning system. The large turbo pumping mechanism 43 couples with the exemplary cleaning chamber 1 and the roughing pumping mechanism 44 couples with the small and large turbo pump mechanisms 9, 43. A roughing pumping mechanism can be any vacuum pump (frequently mechanical) used to initially evacuate a vacuum system, as a first stage towards achieving high vacuum or ultra high vacuum. The term "roughing pump" sometimes derives from the vacuum range it works in, e.g., "rough vacuum", above 1×10–3 torr. The roughing pumping mechanism 44 example in this case can be a scroll pump, given such pumps do not use oil which can contaminate test results.

Figure 4:
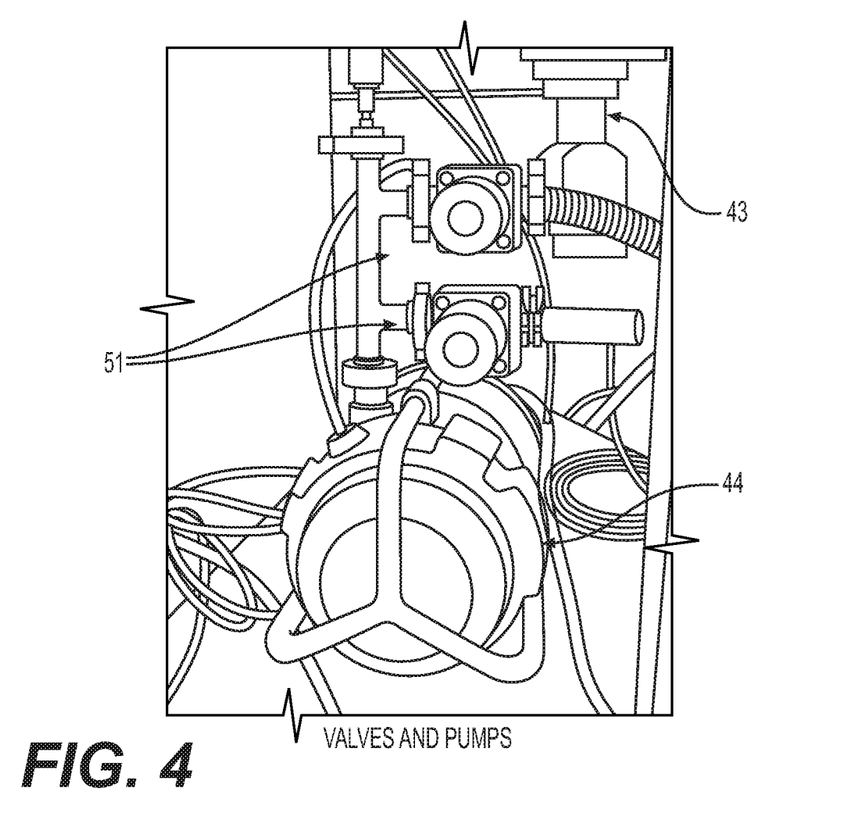
FIG. 4 shows valves and pumps as part of one embodiment of the invention.

Referring to FIG. 4, valves and pumps are shown as part of one exemplary embodiment of an exemplary cleaning system. Valves 51 can be used to maintain and cycle pressure within the exemplary plasma cleaning system. A large turbo pumping mechanism 43 and secondary pumping mechanisms 44 (e.g., roughing or scroll pump) provide low pressure or higher vacuum within various embodiments of an exemplary plasma cleaning system.

Figure 5:
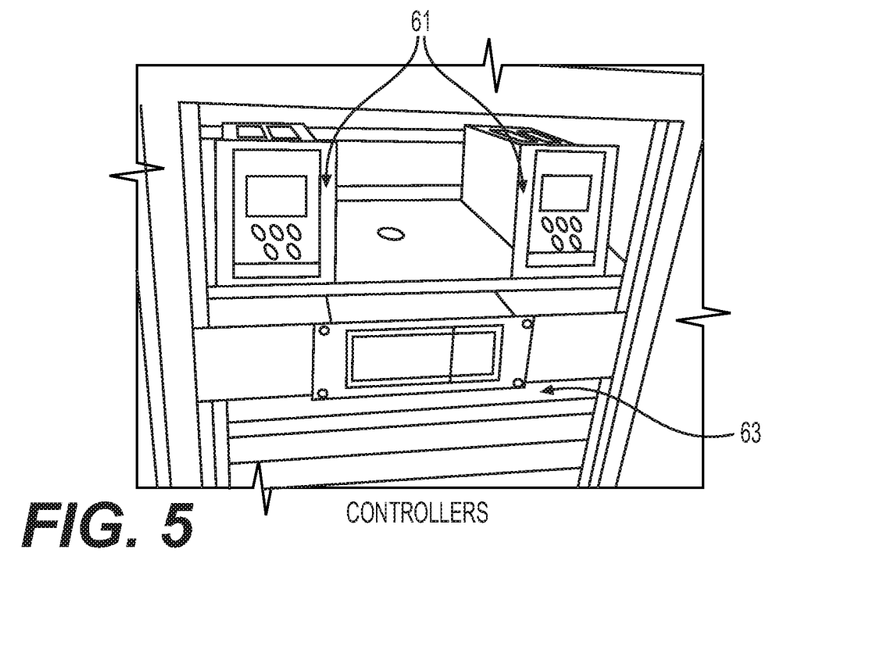
FIG. 5 shows pump controllers and an ion gauge controller are shown as part of one embodiment of the invention.

Referring to FIG. 5, pump controllers and an ion gauge controller are shown as part of the exemplary cleaning system. Pump controllers 61 can be used to control parameters of the pumping system. An ion gauge controller 63 can be used to control parameters and monitor environment conditions. A plasma and gas analyzer control system (not shown) is also provided which controls the gas analyzer 5 and the plasma generator 7 using installed software and/or control hardware.

Figure 6:
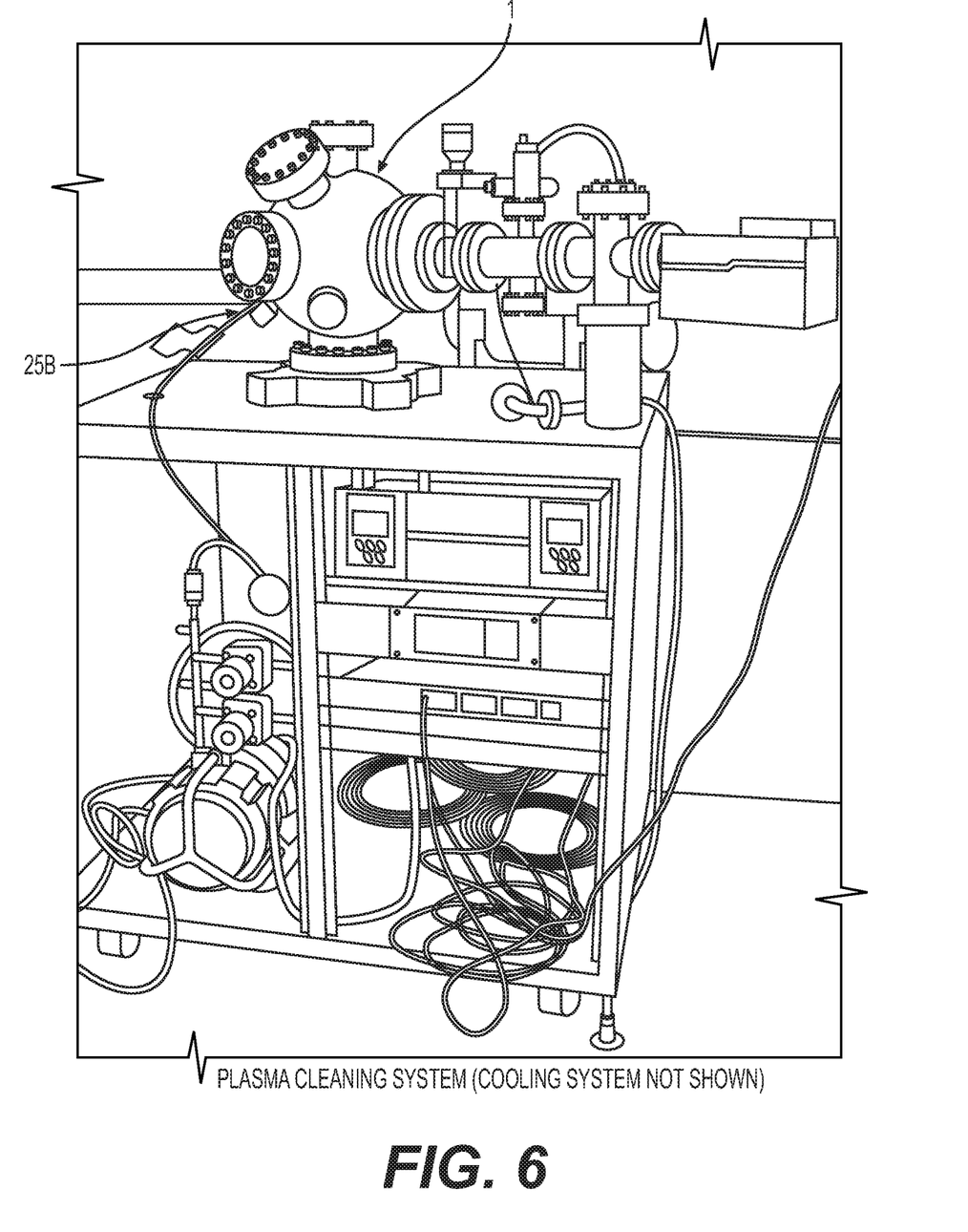
FIG. 6 shows an exemplary apparatus in accordance with one embodiment of the invention.

Referring to FIG. 6, an exemplary cleaning system is shown. This figure does not show a cooling system used to support a pumping system and a plasma generator. Another ion gauge 25B is provided coupled with the cleaning chamber 1 to provide additional vacuum measurements of environments within the cleaning chamber 1.

Generally, an exemplary method of operating an exemplary cleaning system can begin with connecting or coupling an article or item (e.g. pressure gauge) in need of cleaning to or disposing within an exemplary cleaning chamber (e.g. FIG. 1, 1) via a test-connection port in order to expose internal surfaces of the article or item to the cleaning chamber 1 environment. Next, using a pumping system comprised of a scroll pump (e.g., FIG. 3, 44) and a turbo pump, e.g., FIG. 3, 43), sequentially lowering pressure of the cleaning chamber 1. Next, utilizing controllers (e.g., 61 and 63) and gauges (e.g. ion, FIG. 6, 25B, thermocouple, FIG. 3, 41), controlling parameters and monitoring environment conditions in various sections of the cleaning system. Next, using a gas analyzer (e.g., FIG. 1, 5) to monitor and measure chamber gases. Next, a valve system, including a gate valve (e.g., FIG. 2, 23) and leak valve (e.g., FIG. 2, 21,), can be used to maintain and cycle pressure within the cleaning chamber (FIG. 1, 1) and the article or item being cleaned. Next, introducing and regulating reactant and optionally carrier gases into a reactive substance source generator, e.g., a plasma generator (e.g., FIG. 1, 7) to produce reactive substance(s). Next, delivering carrier gas(es) (optional) and the reactive substance(s), e.g., gas(es) comprising activated reactant gas or ionized reactant gas or gases or other cleaning gas or gases which react with identified contaminants (hereinafter reactive substances) into cleaning chamber 1 from plasma generator 7 by creating regions of differential vacuum or pressures (higher vacuum in cleaning chamber 1 than plasma generator 7) via valves (e.g., valves, FIG. 4, 51) using the pumping system (e.g., FIG. 3, 44, 43). After insertion of the reactive substance(s), in this example reactive gas or gases, the reactive gas or gases reacts with the contaminants (e.g. hydrocarbons) on exposed internal or external surfaces of the article or item contained within or attached to cleaning chamber 1. Production of additional vacuum by e.g. turbo pump (item 9, FIG. 2) and cycling of valves (e.g. gate valve (item 23, FIG. 2) and leak valve (item 21, FIG. 2)) can next be used to evacuate gases and reaction byproducts from the cleaning chamber 1 into analysis chamber 3, (FIG. 1). In this example, the item or article is coupled to the cleaning chamber 1 via a port. In other examples, the article or item can be placed into the chamber or in another way which can expose the item or article to the reactive substance flows. The reactive gas will react with the contaminants (e.g. hydrocarbons) on the article or item's exposed surfaces. In some embodiments, the reactive substances such as plasma or ionized reactant gases will have their energy level or exposure times controlled to react with the contaminants to remove some or all of the contaminants. In one example, a staged flow or cycling of pressure is used to introduce and then evacuate the reactive gas or gases into and out of the item or article's exposed internal surfaces. Cycling pressure between sections of the cleaning system can create a pressure differential used to create the staged flow into and out of selected chamber(s) including the cleaning chamber 1 coupled to or containing the item or article. In other words, creating a first vacuum level in the cleaning chamber 1 which is coupled to the article or item, then passing the reactive gas or gases into the cleaning chamber 1 causing the reactive gas or gases to then flow throughout the cleaning chamber 1 and into the article or item as higher pressure reactive gas or gases will flow into lower pressure/higher vacuum voids. In at least some embodiments, exemplary transfer cycling can be accomplished when pressure or vacuum level is alternated between, e.g., plasma generator 7 and cleaning chamber 1 (or analysis chamber 3) to create a movement of reactive substances such as reactive gas or gases. A sample of the cleaning chamber 1 environment can be brought into the analysis chamber (e.g., FIG. 1, 3) through a sampling device (e.g. leak valve 21). Next, a gas analyzer 5 can be used to monitor and measure the cleaning chamber 1 environment sample introduced into the analysis chamber 3. Processing can continue to monitor environment conditions of different sections of the system including the cleaning chamber 1 and indirectly contaminants on or within the item or article to determine changes in composition of materials within the cleaning chamber 1. At some point, an operator can determine a level of cleanliness (e.g. removal of contaminants) of the article or item based on creation of reaction byproducts or contaminant composition changes (e.g. using partial pressure measurements and analysis of gas analyzer 5 output). When cleaning is completed, an operator and/or controller(s) can operate the cleaning system elements to vent and remove gases within the cleaning chamber outside the cleaning system. Once processing is completed, then an operator or machine automation can remove the article or item from the cleaning chamber 1.

Figure 7A:
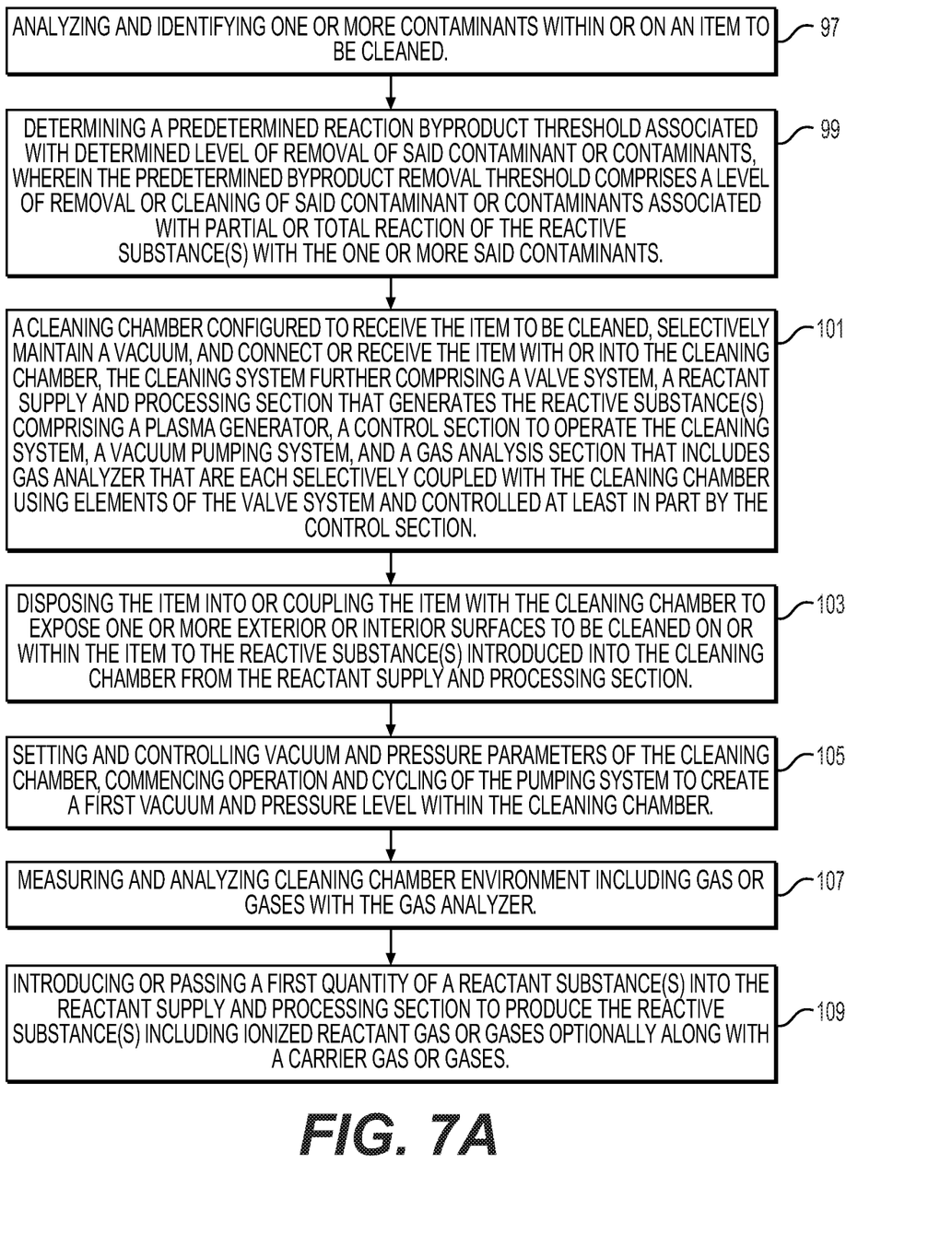
FIGS. 7A and 7B shows a method in accordance with one embodiment of the invention.
Figure 7B:
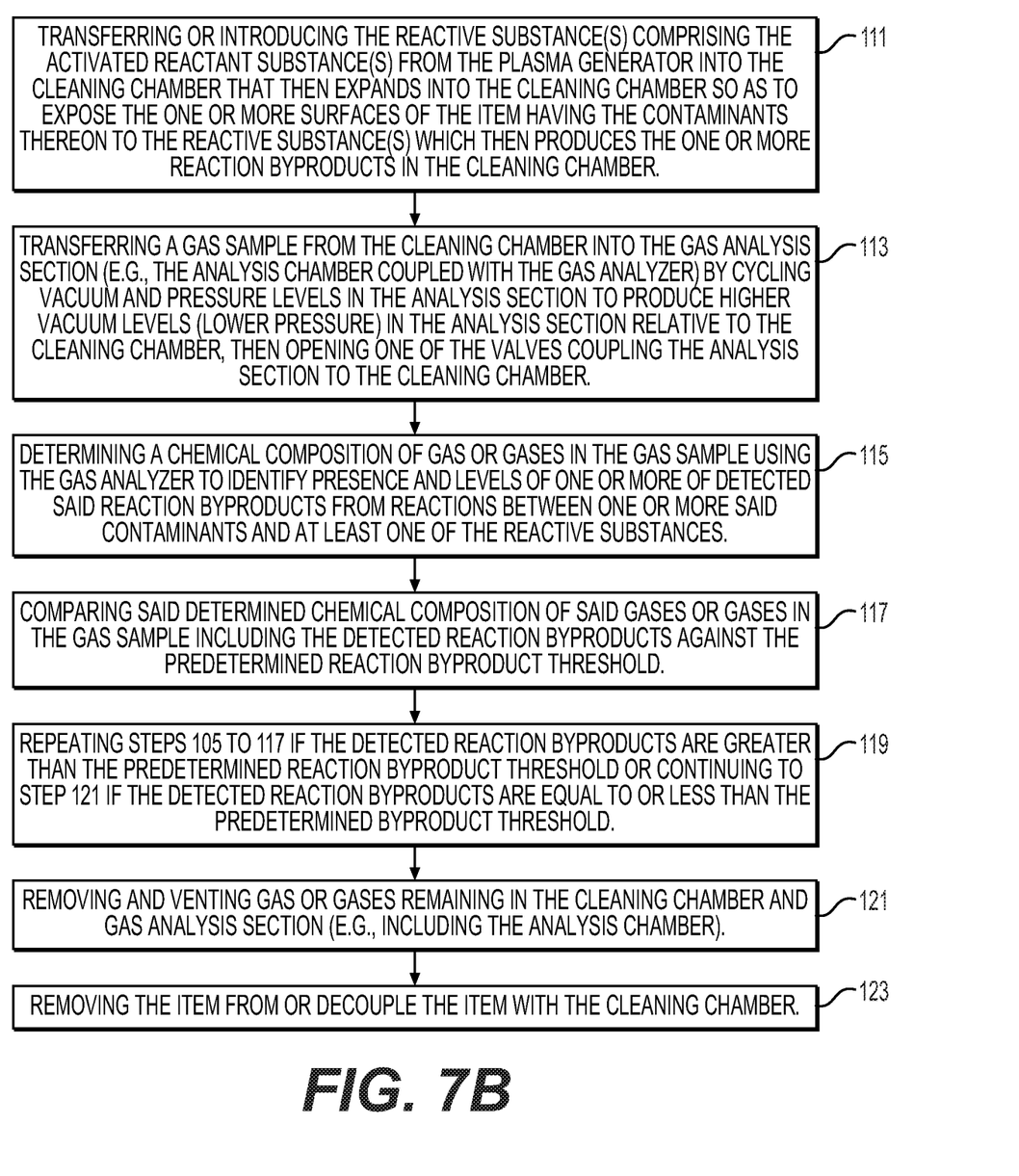

Referring to FIGS. 7A and 7B, a method in accordance with one embodiment of the invention is shown. Referring to FIG. 7A, at Step 97: analyzing and identifying one or more contaminants within or on an item to be cleaned. At Step 99: identifying one or more reactive substances comprising a reactive gas or gases which reacts with the one or more contaminants that produces one or more reaction byproducts and removal or reduction of a presence of the one or more contaminants, Step 99 further comprises determining a predetermined reaction byproduct threshold associated with determined level of removal of said contaminant or contaminants, wherein the predetermined byproduct removal threshold comprises a level of removal or cleaning of said contaminant or contaminants associated with partial or total reaction of the reactive substance(s) with the one or more said contaminants. At Step 101: providing a cleaning system comprising a cleaning chamber configured to receive the item to be cleaned, selectively maintain a vacuum, and connect or receive the item with or into the cleaning chamber, the cleaning system further comprising a valve system, a reactant supply and processing section that generates the reactive substance(s) comprising a plasma generator, a control section operable to operate the cleaning system, a vacuum pumping system, and a gas analysis section that includes gas analyzer that are each selectively coupled with the cleaning chamber using elements of the valve system and controlled at least in part by the control section. At Step 103: disposing the item into or coupling the item with the cleaning chamber to expose one or more exterior or interior surfaces to be cleaned on or within the item to the reactive substance(s) introduced into the cleaning chamber from the reactant supply and processing section. At Step 105: setting and controlling vacuum and pressure parameters of the cleaning chamber, commencing operation and cycling of the pumping system to a create a first vacuum and pressure level within the cleaning chamber. At Step 107: measuring and analyzing cleaning chamber environment including gas or gases with the gas analyzer. Step 107 can be used, for example, to perform an initial test or calibration step. At Step 109: introducing or passing a first quantity of a reactant substance(s) into the reactant supply and processing section to produce the reactive substance(s) including ionized reactant gas or gases optionally along with a carrier gas or gases.

Referring to FIG. 7B, at Step 111: comprising transferring or introducing the reactive substance(s) comprising the activated reactant substance(s) from the plasma generator into the cleaning chamber that then expands into the cleaning chamber so as to expose the one or more surfaces of the item having the contaminants thereon to the reactive substance(s) which then produces the one or more reaction byproducts in the cleaning chamber. At Step 113: transferring a gas sample from the cleaning chamber into the gas analysis section (e.g., the analysis chamber coupled with the gas analyzer) by cycling vacuum level in the analysis section to a higher vacuum level than a cleaning chamber vacuum level, then opening one of the valves coupling the analysis section to the cleaning chamber. At Step 115: determining a chemical composition of gas or gases in the gas sample using the gas analyzer to identify presence and levels of one or more of detected said reaction byproducts from reactions between one or more said contaminants and at least one of the reactive substances. At Step 117: comparing said determined chemical composition of said gases or gases in the gas sample including the detected reaction byproducts against the predetermined reaction byproduct threshold. At Step 119: repeating Step 105 to 117 if the detected reaction byproducts are greater than the predetermined reaction byproduct threshold or continuing to Step 121 if the detected reaction byproducts are equal to or less than the predetermined byproduct threshold. At Step 121: removing and venting gas or gases remaining in the cleaning chamber and gas analysis section (e.g., including the analysis chamber). At Step 123: removing the item from or decouple the item with the cleaning chamber.

Figure 8A:
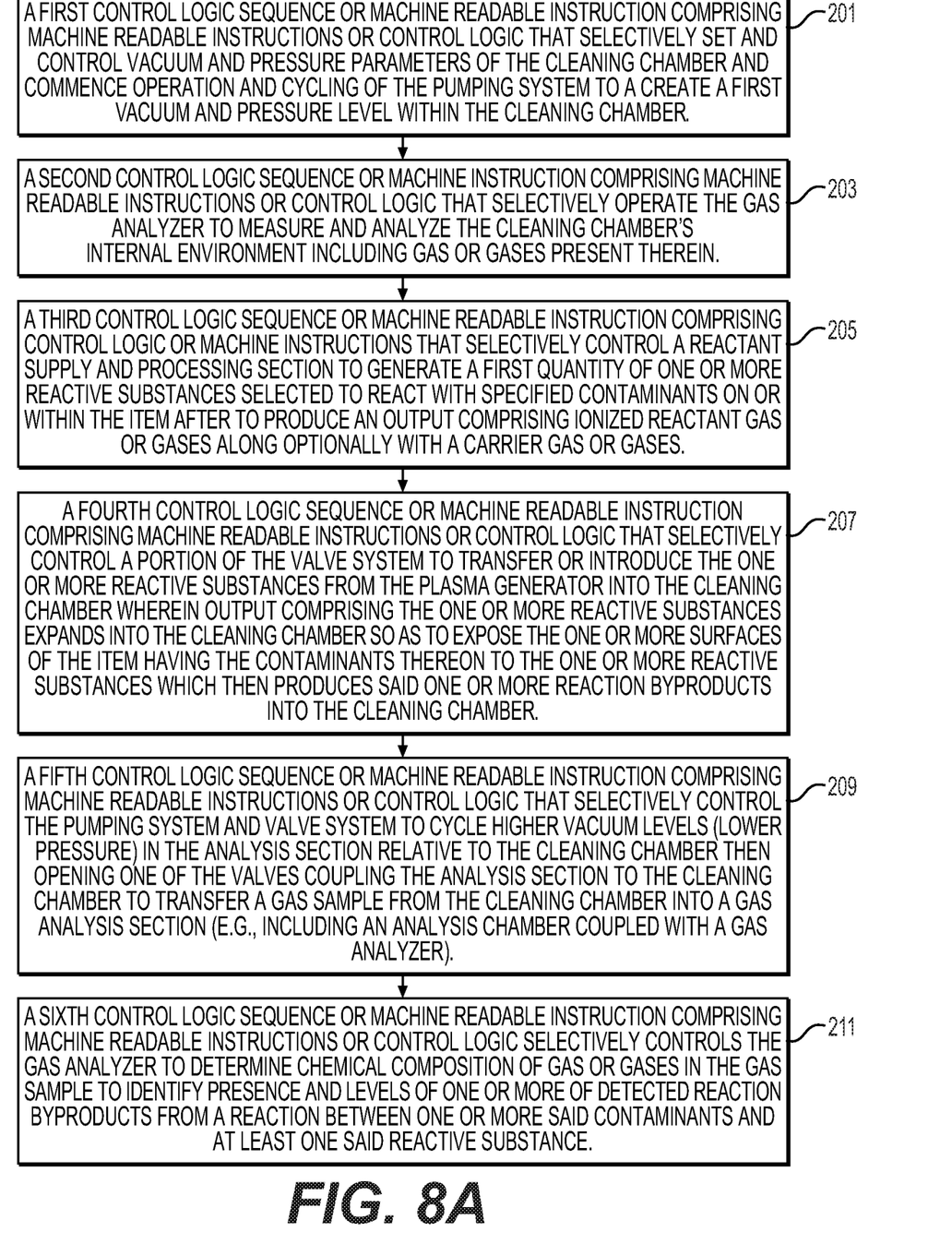
FIGS. 8A and 8B shows a simplified set of control logic sequences or machine readable instructions in accordance with one embodiment of the invention.
Figure 8B:
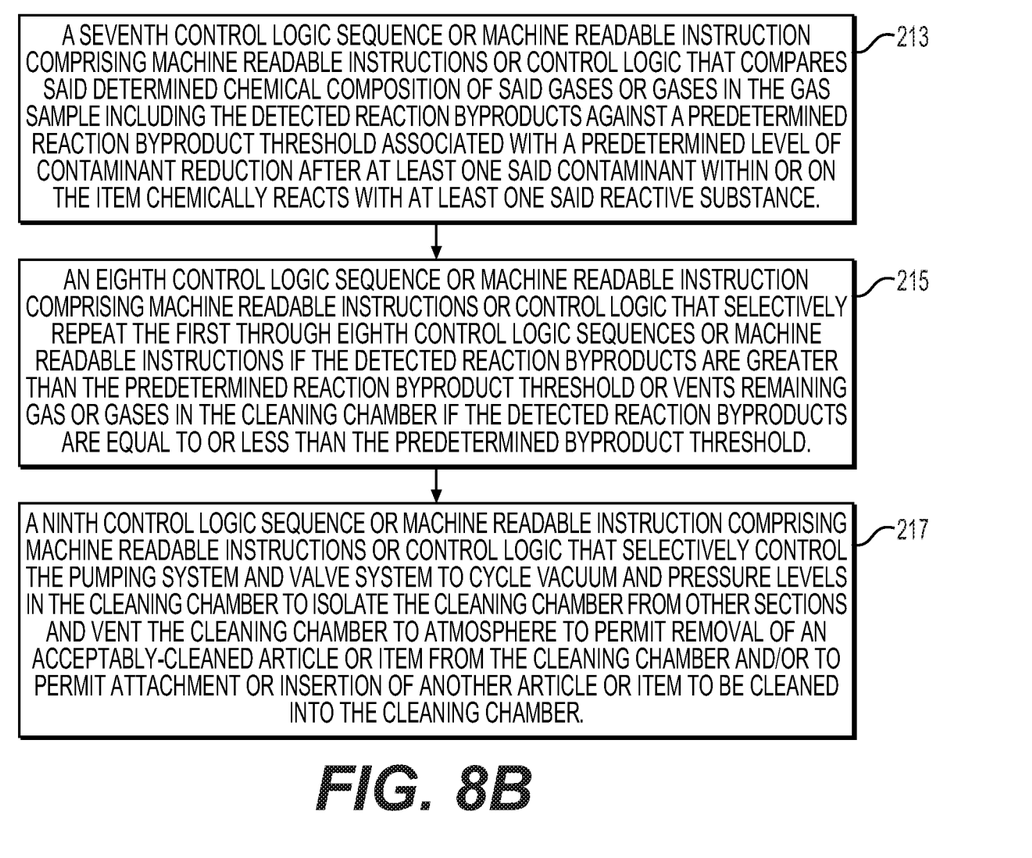

Referring to FIGS. 8A-8B, a simplified set of control logic sequences or machine readable instructions are shown. A first control logic sequence or machine readable instruction 201 comprising machine readable instructions or control logic that selectively set and control vacuum and pressure parameters of the cleaning chamber and commence operation and cycling of the pumping system to a create a first vacuum and pressure level within the cleaning chamber is provided. A second control logic sequence or machine instruction 203 comprising machine readable instructions or control logic that selectively operate the gas analyzer to measure and analyze the cleaning chamber's internal environment including gas or gases present therein is provided. A third control logic sequence or machine readable instruction 205 comprising control logic or machine instructions that selectively controls a reactant supply and processing section to generate a first quantity of reactive substance(s) selected to react with specified contaminants on or within the item to produce an output comprising ionized reactant gas or gases along optionally with a carrier gas or gases is also provided. A fourth control logic sequence or machine readable instruction 207 comprising machine readable instructions or control logic that selectively control a portion of the valve system to transfer or introduce the one or more reactive substances from the plasma generator into the cleaning chamber wherein output comprising the one or more reactive substances expands into the cleaning chamber so as to expose the one or more surfaces of the item having the contaminants thereon to the one or more reactive substances which then produces said one or more reaction byproducts into the cleaning chamber. A fifth control logic sequence or machine readable instruction 209 comprising machine readable instructions or control logic that selectively control the pumping system and valve system to cycle vacuum and pressure levels in the analysis section to a lower level than pressure and vacuum level in the cleaning chamber, then opening one of the valves coupling the analysis section to the cleaning chamber after said reactive substance reacts with at least one said contaminant to transfer a gas sample from the cleaning chamber into a gas analysis section (e.g., including an analysis chamber coupled with a gas analyzer) is also provided. A sixth control logic sequence or machine readable instruction comprising machine readable instructions or control logic 211 that selectively controls the gas analyzer to determine chemical composition of gas or gases in the gas sample to identify presence and levels of one or more of detected reaction byproducts from a reaction between one or more said contaminants and at least one said reactive substance is also provided. A seventh control logic sequence or machine readable instruction 213 comprising machine readable instructions or control logic that selectively compares said determined chemical composition of said gas or gases in the gas sample including the detected reaction byproducts against a predetermined reaction byproduct threshold associated with a predetermined level of contaminant reduction after at least one said contaminant within or on the item chemically reacts with at least one said reactive substance is also provided. An eighth control logic sequence or machine readable instruction 215 comprising machine readable instructions or control logic that selectively repeat the first through eighth control logic sequences or machine readable instructions if the detected reaction byproducts are greater than the predetermined reaction byproduct threshold or vents remaining gas or gases in the cleaning chamber if the detected reaction byproducts are equal to or less than the predetermined byproduct threshold. A ninth control logic sequence or machine readable instruction comprising machine readable instructions or control logic 217 that selectively control the pumping system and valve system to cycle vacuum and pressure levels in the cleaning chamber to isolate the cleaning chamber from other sections and vent the cleaning chamber to atmosphere to permit removal of an acceptably-cleaned article or item from the cleaning chamber and/or to permit attachment or insertion of another article or item to be cleaned into the cleaning chamber.

Figure 9:
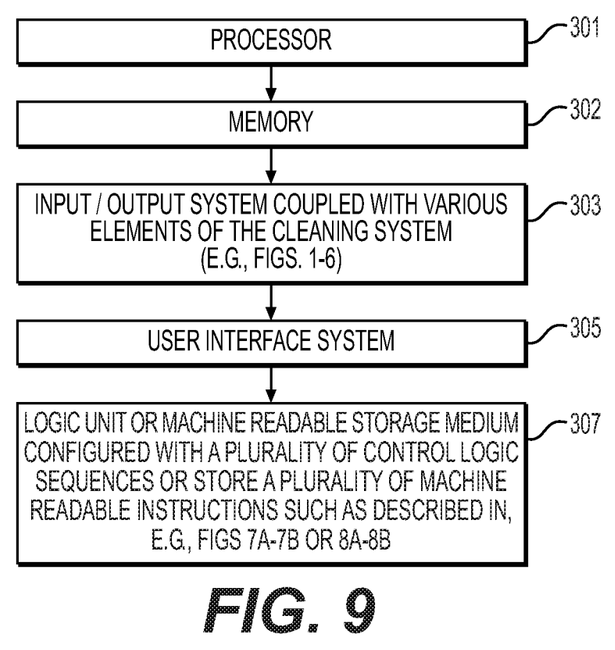
FIG. 9 shows an exemplary embodiment of a simplified control system or section is shown that performs various control operations for the cleaning system in accordance with one embodiment of the invention.

Referring to FIG. 9, an exemplary embodiment of a simplified control system or section is shown that performs various control operations for the cleaning system is shown. A processor 301, memory 302, Input/Output System coupled with various elements of the cleaning system (e.g., FIGS. 1-6) 303, a User Interface System 305, Logic Unit or Machine Readable Storage Medium configured with a plurality of control logic sequences or store and execute (e.g., via the processor) a plurality of machine readable instructions such as described in, e.g., FIGS. 7A-7B or 8A-8B 307 is shown.

In a variety of embodiments, broadly speaking, a given reactant gas, material or substance input that various embodiments of the invention can be configured to receive and process can include a "raw material" from which the reactive substance or activated reactant gas is created/made/produced by the reactant source generator, e.g., a plasma generator, that performs a desired reactant cleaning function with an identified contaminant associated with an exemplary item to be cleaned. Also, an exemplary plasma generator would not necessarily convert all of the reactant gas into an activated form (e.g., ionized reactant gas). Additionally, in various embodiments reactive substances or activated reactant gas(es), material(s) or substance(s) entering the cleaning chamber to perform reactant cleaning by, e.g., differential pressure or vacuum cycling, can be a mixture of (unreacted/unconverted) reactant gas(es), materials or substances and activated reactant gas(es), materials, or substances. Reactive substances or activated reactant gas(es), substance(s), or material(s) inputs can also include other compounds that perform a reactive function with identified contaminants such as free radicals (e.g., an uncharged molecule or atom (typically highly reactive and short-lived) having an unpaired valence (i.e., outer shell) electron such as, e.g., a single oxygen atom having no charge (not an ion) created from a diatomic oxygen combination (e.g. O2) which an exemplary plasma generator can create by breaking apart the O2 or diatomic oxygen molecule). Thus, in at least some embodiments such reactive substances or activated reactant gas(es), substance(s), or material(s) can be more than just ionized reactive substance inputs that are conveyed into the cleaning chamber to reactively clean contaminants on or within the item to be cleaned. Note that such reactive or activated reactant gas(es), material(s) or substances can also be selected based on whether or not they cause damage to the item to be cleaned or a degree of damage found acceptable as well as other selection factors such as environmental impacts, cost, safety/hazardous properties (e.g., harm to humans or animals), availability, and other logistics considerations. Additional sources of reactive substances or activated reactive materials, substances, or gas(es) can be provided in place of or in combination with the plasma generator such an ozone injection source that selectively injects ozone into the cleaning chamber upon determination of presence of an organic contaminant in the item to be cleaned and a determination that the additional or alternative reactive substances or activated reactive materials, substances, or gas(es) will not cause damage beyond a predetermined limit to the item to be cleaned. For example, ozone can be selected as a reactive substance or gas that reacts with organic materials where the ozone will oxidize the organic materials. Accordingly, an alternative embodiment may include a system that has the plasma generator replaced with another reactive substance generator such as the ozone generator or injector. Another alternative embodiment can include an addition of the alternative reactive substance or activated reactant material(s), gas(es), or substance(s) source in addition to the plasma generator. Yet another embodiment can include a control section that selectively uses the alternative reactive substance or activated reactant material(s), gas(es), or substance(s) source, e.g., ozone generator, and uses a combination of such sources based on outputs of the gas analyzer during cleaning operations to provide a sequence of varying sources inputs to achieve a desired level of contaminant reduction where a single such source may not be fully effective to meet predetermined cleaning levels. For example, a controls section might use one source over a predetermined number of differential pressure cycles (e.g., cleaning and analysis) then add or switch to another reactive substance or activated reactant source (e.g., ozone) of a first reaction byproduct threshold it not met and then perform additional cycles of cleaning and analysis using a second reactive substance or activated reactant material(s), gas(es), or substance(s) source until a second reaction byproduct threshold is met.

Although the invention has been described in detail with reference to certain preferred embodiments, variations and modifications exist within the spirit and scope of the invention as described and defined in the following claims.

The invention claimed is:

1. A method for producing a plasma cleaning system, comprising:

executing a first step comprising analyzing and identifying one or more contaminants within a partially enclosed interior section of an item to be cleaned, wherein the partially enclosed interior section is accessible through an aperture or port in an external section of the item to be cleaned;

executing a second step comprising identifying one or more activated reactant or reactive substances comprising one or more activated reactants or reactive gas(es), materials, or substances that reacts with the one or more contaminants that produces one or more reaction byproducts and removal or reduction of a presence of the one or more contaminants, said second step further comprises determining a predetermined reaction byproduct threshold associated with a pre-selected level of removal of said contaminant or contaminants;

executing a third step comprising providing a cleaning system comprising a cleaning chamber configured to receive the item to be cleaned, selectively maintain a vacuum, and connect or receive the item with or into the cleaning chamber, the cleaning system further comprising a valve system, a reactant supply and processing section which includes a plasma generator that generates or supplies said reactive substance or activated reactant comprising a reactive gas or gases, a control section operable to operate the cleaning system, a vacuum pumping system, and a gas analysis section that includes a gas analyzer that are each selectively coupled with the cleaning chamber using coupling elements comprising the valve system and controlled at least in part by the control section;

executing a fourth step comprising disposing the item into or coupling the item with the cleaning chamber to expose one or more interior surfaces to be cleaned associated with said partially enclosed interior section within the item to the reactive substances;

executing a fifth step comprising setting and controlling vacuum and pressure parameters of the cleaning chamber, commencing operation and cycling of the pumping system to create a first vacuum and pressure level within the cleaning chamber;

executing a sixth step comprising generating a first quantity of the reactive substance selected to react with the one or more contaminants using the reactant supply and processing section;

executing a seventh step comprising transferring or introducing the one or more reactive substances into the cleaning chamber using one of the valves, wherein the one or more reactive substances then expands into the cleaning chamber and into the partially enclosed interior section through the aperture or port so as to expose the one or more interior surfaces of the item having the contaminants thereon to the one or more reactive substances which then produces said one or more reaction byproducts into the cleaning chamber;

executing an eighth step comprising transferring a gas sample from the cleaning chamber into the gas analysis section by cycling an analysis section vacuum level to a higher vacuum level than a cleaning chamber vacuum level reached after said one or more reactive substances have been introduced into the cleaning chamber after said first vacuum has been achieved in said cleaning chamber, then opening one of the valves coupling the analysis section to the cleaning chamber;

executing a ninth step comprising determining chemical composition of gas or gases in the gas sample using the gas analyzer to identify presence and levels of one or more of detected reaction byproducts from a reaction between one or more said contaminants and at least one said reactive substance;

executing a tenth step comprising comparing said determined chemical composition of said gas or gases in the gas sample including the detected reaction byproducts against the predetermined reaction byproduct threshold;

executing an eleventh step comprising repeating the fifth through eleventh step if the detected reaction byproducts are greater than the predetermined reaction byproduct threshold or continuing to twelfth step if the detected reaction byproducts are equal to or less than the predetermined byproduct threshold;

executing a twelfth step comprising removing and venting gas or gases remaining in the cleaning chamber and the gas analysis section; and removing the item from or decoupling the item with the cleaning chamber;

wherein the item is a Bourdon tube.

2. A method as in claim 1, wherein the predetermined reaction byproduct threshold comprises a predetermined level of removal or cleaning of said contaminant or contaminants associated with partial or total reaction with at least one said reactive substance.

3. A method as in claim 1, where said fifth step further comprises measuring and analyzing the cleaning chamber's internal environment including gas or gases using the gas analyzer to create a reference or calibration value data or comparator.

4. A method as in claim 1, wherein the vacuum pumping system comprises at least one turbo pump and at least one scroll pump that together provides vacuum of down to $10^8$ torr.

5. A method as in claim 1, wherein the cleaning system further comprises a cooling system comprising tubing that delivers cooled water into elements of the vacuum pump system and plasma generator's heat transfer manifolds or passageways that is adapted to receive a supply of cooling medium or fluid which passes cooled water through some components of the cleaning system including one or more elements of the vacuum pump system comprising a turbo pump.

6. A method as in claim 1, wherein said gas analysis section further comprises an analysis chamber coupled between the cleaning chamber and the gas analyzer, wherein the cleaning system further comprises a first and second ion gage that are respectively configured to measure vacuum levels in the cleaning chamber and the analysis chamber.

7. A method for cleaning an item using a plasma cleaning system, comprising: executing a first step comprising analyzing and identifying one or more contaminants within or on an item to be cleaned;

executing a second step comprising identifying one or more activated reactant or reactive substances comprising one or more activated reactants or reactive gas(es), materials, or substances that reacts with the one or more contaminants that produces one or more reaction byproducts and removal or reduction of a presence of the one or more contaminants, said second step further comprises determining a predetermined reaction byproduct threshold associated with a pre-selected level of removal of said contaminant or contaminants;

executing a third step comprising providing a cleaning system comprising a cleaning chamber configured to receive the item to be cleaned, selectively maintain a vacuum, and connect or receive the item with or into the cleaning chamber, the cleaning system further comprising a valve system, a reactant supply and processing section which includes a plasma generator that generates or supplies said reactive substance or activated reactant comprising a reactive gas or gases, a control section operable to operate the cleaning system, a vacuum pumping system, and a gas analysis section that includes a gas analyzer that are each selectively coupled with the cleaning chamber using coupling elements comprising the valve system and controlled at least in part by the control section;

executing a fourth step comprising disposing the item into or coupling the item with the cleaning chamber to expose one or more exterior or interior surfaces to be cleaned on or within the item to the reactive substances;

executing a fifth step comprising setting and controlling vacuum and pressure parameters of the cleaning chamber, commencing operation and cycling of the pumping system to create a first vacuum and pressure level within the cleaning chamber;

executing a sixth step comprising generating a first quantity of the reactive substance selected to react with the one or more contaminants using the reactant supply and processing section;

executing a seventh step comprising transferring or introducing the one or more reactive substances into the cleaning chamber using one of the valves, wherein the one or more reactive substances then expands into the cleaning chamber so as to expose the one or more surfaces of the item having the contaminants thereon to the one or more reactive substances which then produces said one or more reaction byproducts into the cleaning chamber;

executing an eighth step comprising transferring a gas sample from the cleaning chamber into the gas analysis section by cycling an analysis section vacuum level to a higher vacuum level than a cleaning chamber vacuum level reached after said one or more reactive substances have been introduced into the cleaning chamber after said first vacuum has been achieved in said cleaning chamber, then opening one of the valves coupling the analysis section to the cleaning chamber;

executing a ninth step comprising determining chemical composition of gas or gases in the gas sample using the gas analyzer to identify presence and levels of one or more of detected reaction byproducts from a reaction between one or more said contaminants and at least one said reactive substance;

executing a tenth step comprising comparing said determined chemical composition of said gas or gases in the gas sample including the detected reaction byproducts against the predetermined reaction byproduct threshold;

executing an eleventh step comprising repeating the fifth through eleventh step if the detected reaction byproducts are greater than the predetermined reaction byproduct threshold or continuing to a twelfth step if the detected reaction byproducts are equal to or less than the predetermined byproduct threshold;

executing the twelfth step comprising removing and venting gas or gases remaining in the cleaning chamber and the gas analysis section; and removing the item from or decoupling the item with the cleaning chamber;

wherein the vacuum pumping system comprises at least one turbo pump and at least one scroll pump;

wherein the cleaning system further comprises a cooling system comprising tubing that delivers cooled water into elements of the vacuum pump system and plasma generator's heat transfer manifolds or passageways that is adapted to receive a supply of cooling medium or fluid which passes cooled water through some components of the cleaning system including one or more elements of the vacuum pump system comprising a turbo pump;

wherein said gas analysis section further comprises an analysis chamber coupled between the cleaning chamber and the gas analyzer, wherein the cleaning system further comprises a first and second ion gage that are respectively configured to measure vacuum levels in the cleaning chamber and the analysis chamber;

wherein said item is a Bourdon Tube.

8. A method as in claim 7, wherein the vacuum pumping system provides vacuum of down to $10^8$ torr.

9. A method as in claim 7, wherein the predetermined reaction byproduct threshold comprises a predetermined level of removal or cleaning of said contaminant or contaminants associated with partial or total reaction with at least one said reactive substance.

10. A method as in claim 7, where said fifth step further comprises measuring and analyzing the cleaning chamber's internal environment including gas or gases using the gas analyzer to create a reference or calibration value data or comparator.

* * * * *